(12) United States Patent
Justis et al.

(10) Patent No.: US 7,563,274 B2
(45) Date of Patent: Jul. 21, 2009

(54) SURGICAL INSTRUMENTS AND TECHNIQUES FOR CONTROLLING SPINAL MOTION SEGMENTS WITH POSITIONING OF SPINAL STABILIZATION ELEMENTS

(75) Inventors: Jeff R. Justis, Collierville, TN (US); Fred J. Molz, IV, Birmingham, AL (US); Michael C. Sherman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 330 days.

(21) Appl. No.: 11/410,727

(22) Filed: Apr. 25, 2006

(65) Prior Publication Data

US 2007/0270819 A1 Nov. 22, 2007

(51) Int. Cl.
*A61B 17/88* (2006.01)
*A61B 17/70* (2006.01)
(52) U.S. Cl. .................... 606/279; 606/246
(58) Field of Classification Search .............. 606/61, 606/69, 279, 246, 256, 264, 265, 99, 86 R; 623/17.11–17.16
See application file for complete search history.

(56) References Cited

U.S. PATENT DOCUMENTS

| | | | |
|---|---|---|---|
| 5,282,863 A | 2/1994 | Burton | |
| 5,382,248 A | 1/1995 | Jacobson et al. | |
| 5,415,661 A | 5/1995 | Holmes | |
| 5,527,315 A | 6/1996 | Jeanson et al. | |
| 5,562,660 A | 10/1996 | Grob | |
| 5,593,408 A | 1/1997 | Gayet et al. | |
| 5,630,816 A | 5/1997 | Kambin | |
| 5,658,286 A * | 8/1997 | Sava | 606/61 |
| 6,099,528 A | 8/2000 | Saurat | |
| 6,102,912 A * | 8/2000 | Cazin et al. | 606/61 |
| 6,364,881 B1 * | 4/2002 | Apgar et al. | 606/69 |
| 6,530,929 B1 | 3/2003 | Justis et al. | |
| 6,966,910 B2 | 11/2005 | Ritland | |
| 7,008,424 B2 * | 3/2006 | Teitelbaum | 606/61 |
| 2002/0161368 A1 * | 10/2002 | Foley et al. | 606/61 |
| 2003/0171749 A1 * | 9/2003 | Le Couedic et al. | 606/61 |
| 2003/0191470 A1 | 10/2003 | Ritland | |
| 2003/0220642 A1 | 11/2003 | Freudiger | |
| 2004/0147928 A1 | 7/2004 | Landry et al. | |
| 2004/0215191 A1 | 10/2004 | Kitchen | |
| 2004/0236327 A1 * | 11/2004 | Paul et al. | 606/61 |
| 2005/0065515 A1 * | 3/2005 | Jahng | 606/61 |
| 2005/0136764 A1 | 6/2005 | Sherman et al. | |
| 2005/0215999 A1 | 9/2005 | Birkmeyer et al. | |
| 2006/0064092 A1 | 3/2006 | Howland | |
| 2007/0042633 A1 | 2/2007 | Frigg et al. | |
| 2007/0191841 A1 | 8/2007 | Justis et al. | |

FOREIGN PATENT DOCUMENTS

| | | |
|---|---|---|
| EP | 0 301 489 A | 2/1989 |
| EP | 1 364 622 A2 | 11/2003 |
| WO | WO 2005/084566 | 9/2005 |

* cited by examiner

*Primary Examiner*—Pedro Philogene

(57) ABSTRACT

Elongated connecting elements include bodies having anisotropic cross-sectional shapes defining a first moment of inertia about a first bending axis and a second moment of inertia about a second bending axis that is transverse to the first bending axis. The connecting elements are positioned along one or more spinal motion segments and engaged to vertebrae with anchors with the first and second bending axes in the desired orientation relative to the spinal motion segments.

30 Claims, 9 Drawing Sheets

SURGICAL INSTRUMENTS AND TECHNIQUES FOR CONTROLLING SPINAL MOTION SEGMENTS WITH POSITIONING OF SPINAL STABILIZATION ELEMENTS

BACKGROUND

Various devices and methods for stabilizing bone structures have been used for many years. For example, one type of stabilization technique uses one or more elongated rods extending between components of a bony structure and secured to the bony structure to stabilize the components relative to one another. The components of the bony structure are exposed and one or more bone engaging fasteners are placed into each component. The elongated rod is then secured to the bone engaging fasteners in order to stabilize the components of the bony structure.

One problem associated with the above described stabilization structures is that the stabilization structure can provide the same stabilization effect in all planes of motion of a spinal motion segment. In addition, skin and tissue surrounding the surgical site must be cut, removed, and/or repositioned in order for the surgeon to access the location where the stabilization device is to be installed. This repositioning of tissue causes trauma, damage, and scarring to the tissue. There are also risks that the tissue will become infected and that a long recovery time will be required after surgery for the tissue to heal. There remains a need for further improvements in instruments and methods for stabilizing one or more motion segments of the spinal column.

SUMMARY

Elongated connecting elements include bodies having anisotropic cross-sectional shapes defining a first moment of inertia about a first bending axis and a second moment of inertia about a second bending axis that is transverse to the first bending axis. The connecting elements are positioned along one or more spinal motion segments and engaged to vertebrae with anchors with the first and second bending axes in the desired orientation relative to the spinal motion segments.

According to one aspect, a system for spinal stabilization includes a first anchor engageable to a first vertebral body with a bone engaging portion for engaging the first vertebral body along a first engagement axis and a second anchor engageable to a second vertebral body with a bone engaging portion engaging the second vertebral body along a second engagement axis. A connecting element includes an elongated body extending between opposite first and second ends and is positionable between and engageable to each of the first and second anchors. The elongated body includes an anisotropic cross-sectional shape defining a first bending axis and a second bending axis transversely oriented to the first bending axis. The body includes a first moment of inertia about the first bending axis and a second moment of inertia about the second bending axis that differs from the first moment of inertia. A selected one of the first and second bending axes is aligned in the direction of the first and second engagement axes and the connecting element is engaged to the first and second anchors in the aligned orientation.

According to another aspect, a system for spinal stabilization includes a first anchor engageable to a first vertebral body with a bone engaging portion for engaging the first vertebral body along a first engagement axis and a second anchor engageable to a second vertebral body with a bone engaging portion for engaging the second vertebral body along a second engagement axis. The system includes a first anchor extension including a distal end releasably engageable to the first anchor and an elongated body extending proximally from the distal end to a proximal end. The system also includes a second anchor extension including a distal end releasably engageable to the second anchor and an elongated body extending proximally from the distal end to a proximal end. The system further includes an inserter instrument and a connecting element releasably engaged to the inserter instrument. The connecting element includes an elongated body positionable between and engageable to each of the first and second anchors. The elongated body of the connecting element includes an anisotropic cross-sectional shape defining a first bending axis and a second bending axis transversely oriented to the first bending axis. The body of the connecting element includes a first moment of inertia about the first bending axis and a second moment of inertia about the second bending axis that differs from the first moment of inertia. The inserter instrument can be engaged with the connecting element with a selected one of the first and second bending axes in a predetermined orientation relative to the first and second engagement axes of the first and second anchors. The inserter instrument is operable to move the connecting element while maintaining the predetermined orientation from a location remote from the first and second anchors to a location adjacent the first and second anchors for engagement of the connecting element to the first and second anchors in the predetermined orientation.

According to another aspect, a method for stabilizing at least one spinal motion segment comprises: engaging a first anchor to a first vertebral body; engaging a second anchor to a second vertebral body; providing a connecting element, wherein the connecting element includes an elongated body having a cross-sectional shape defining a first moment of inertia about a first bending axis and a second moment of inertia about a second bending axis that is transverse to the first bending axis; selecting an orientation of the first and second bending axes relative to the first and second vertebral bodies; positioning the connecting element in the selected orientation between the first and second anchors; and engaging the connecting element to the first and second anchors with the connecting element positioned in the orientation.

In another aspect, a connecting element for positioning along a spinal column includes an elongated body extending along a longitudinal axis between a first end and an opposite second end. The body includes at least one stabilization portion extending along the longitudinal axis that has an anisotropic cross-section orthogonally to the longitudinal axis. The elongated body also includes at least one connecting portion along the longitudinal axis that has a circular cross-section orthogonally to the longitudinal axis. The connecting portion has a length sized to engage a spinal anchor engageable to a spinal column and the stabilization portion has a length sized to extend along at least one vertebra.

In yet another aspect, a connecting element for positioning along a spinal column includes an elongated body extending along a longitudinal axis between a first end and an opposite second end. The body has a length sized to extend between at least two vertebrae of the spinal column and includes a circular cross-section in a plane taken orthogonally to the longitudinal axis. The body further includes a lumen extending at least partially along the length of the body that has a non-circular cross-section orthogonal to the longitudinal axis. The body includes a first moment of inertia about a first bending axis along the cross-section and a second moment of inertia about a second bending axis along the cross-section that is orthogonal to the first bending axis.

Related features, aspects, embodiments, objects and advantages of the present invention will be apparent from the following description.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

A connecting element for connection with anchors engaged to one or more vertebral bodies is provided with an anisotropic cross-section extending along all or a substantial portion of a length of a body of the connecting element. The anisotropic cross-section can provide a greater resistance to bending in a first direction than in a second direction. The connecting element can include a moment of inertia about a first bending axis along the cross-section that extends in a first direction relative to a vertebral body when secured along one or more spinal motion segments. The connecting element can also include a second moment of inertia about a second bending axis along the cross-section that extends in a second direction relative to the vertebral body when the connecting element is secured along one or more spinal motion segments. The moments of inertia differ from one another to provide the body of the connecting element with differing stiffness characteristics about different planes of motion of the spinal motion segment. Other moments of inertia about other bending axes that are the same as or that differ from the first and second moments of inertia are also contemplated.

In one example, the connecting element can be positioned along the spinal column so that the first bending axis is oriented to resist lateral bending of one or more motion segments of the spinal column, while the second bending axis is positioned to resist extension and flexion of one or more motion segments of the spinal column. In another example, the connecting element can be positioned along the spinal column so that the first bending axis is oriented to resist extension and flexion of one or more motion segments of the spinal column, while the second bending axis is positioned to resist lateral bending of one or more motion segments of the spinal column. Other orientations of the bending axes relative to the planes of motion of the spinal motion segment or segments are also contemplated.

The connecting element can be positioned into the patient in minimally invasive surgical procedures with a system that percutaneously guides the connecting element into the patient along a minimally invasive insertion path to one or more anchors with the first and second bending axes in a predetermined orientation relative to the spinal motion segment. The connecting element can be maintained in the predetermined orientation as it is inserted and then secured in engagement with the spinal motion segment in the predetermined orientation with anchors engaged to the spinal motion segment. Other embodiments contemplate that the connecting element is inserted into the patient and thereafter aligned to provide a predetermined orientation of the bending axis relative to the spinal motion segment.

Figure 1A:
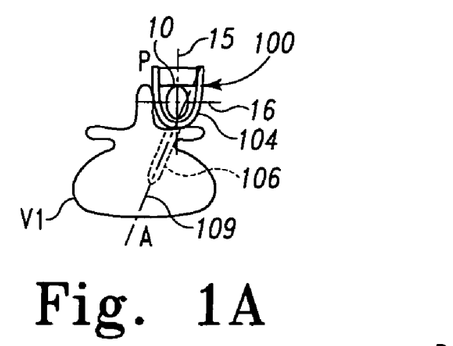
FIGS. 1A, 1B, and 1C are diagrammatic views show various attachment arrangements for securing a connecting element along the spinal column with an anchor.

As shown in FIG. 1A, an elongated connecting element 10 can be secured to vertebral body V1 with one or more anchors 100 with the connecting element extending along one or more spinal motion segments. Connecting element 10 is understood to be any of the connecting element embodiments discussed herein, and has an anisotropic cross-section including a first bending axis 15 defining a first moment of inertia thereabout. The cross-section of connecting element 10 also includes a second bending axis 16 transverse to the first bending axis 15 that defines a second moment of inertia thereabout that differs from the first moment of inertia.

Anchor 100 includes a receiver 104 for receiving connecting element 10 therein, and a bone engaging portion 106 for engaging a vertebral body V1. Bone engaging portion 106 can be a threaded screw-like member that extends into and engages the bony structure of vertebral body V1. Other embodiments contemplate that anchor 100 can include a bone engaging portion in the form of a hook, staple, bolt, cable, or other suitable bone engaging device. Receiver 106 can include a pair of arms defining a passage therebetween for receiving the connecting element. The arms can be top-loading as shown and internally and/or externally threaded to engage a set screw or other engaging member. Other embodiments contemplate receivers that are side-loading, bottom loading, end-loading, clamping members, or any other suitable arrangement for securing connecting element 10 along the spinal column.

In FIG. 1A anchor 100 includes an engagement axis 109 extending toward vertebral body V1 in a generally posterior P to anterior A direction. Bone engaging portion 106 extends in the direction of an engagement axis 109 to engage vertebral body V1. Bone engaging portion 106 is shown engaged through the pedicle of vertebral body V1. When connecting element 10 is positioned in receiver 104, first bending axis IS extends toward vertebral body V1 in the same general direction as engagement axis 109. Second bending axis 16 is transversely oriented to first bending axis 15, and extends tangentially to or along the pedicles of vertebral body V1.

Figure 1B:
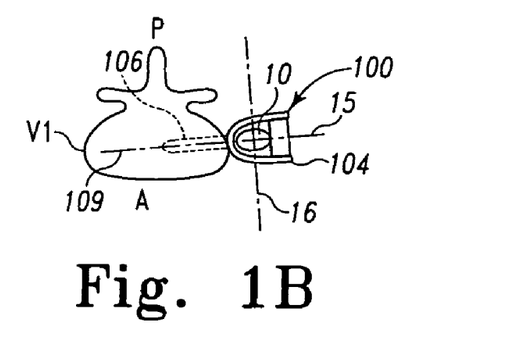
Figure 1C:
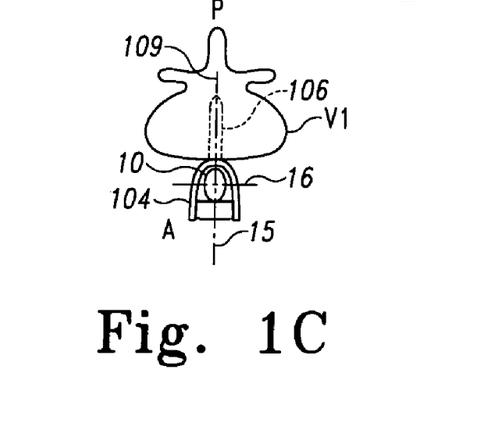

In FIG. 1B, connecting element 10 is engaged laterally along vertebral body V1 with anchor 100 having engagement axis 109 extending into vertebral body V1 in a medial-lateral direction. First bending axis 15 extends along engagement axis 109, and second bending axis 16 extends tangentially to vertebral body V1 along its lateral face. In FIG. 1C, connecting element 10 is engaged anteriorly along vertebral body V1 with anchor 100 having engagement axis 109 extending into vertebral body V1 in an anterior-posterior direction. First bending axis 15 extends along engagement axis 109, and second bending axis 16 extends tangentially to vertebral body V1 along its anterior face. Other embodiments contemplated that connecting element 10 could be engaged along an oblique face of the vertebral body or to posterior elements of the vertebral body.

Figures 1D, 1E:
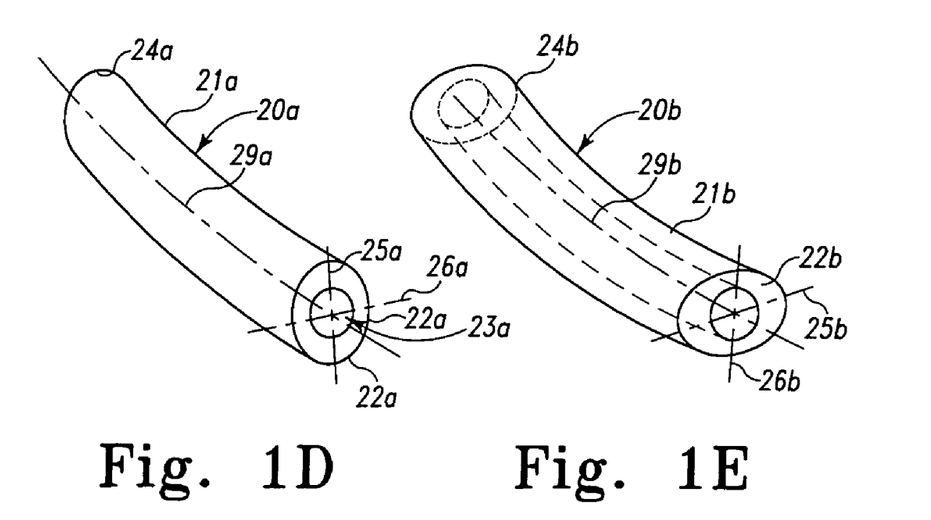
FIGS. 1D and 1E are perspective views of one embodiment connecting element in first and second implantation orientations, respectively.

FIG. 1D shows one embodiment of connecting element 10 in the form of connecting element 20a for engagement along one or more spinal motion segments with one or more anchors 100. Connecting element 20a has an anisotropic cross-section provided by a non-circular outer perimeter. Connecting element 20a includes an elongated body 21a extending along longitudinal axis 29a between a first end 22a and an opposite second end 24a. Body 21a can also define a central lumen 23a extending longitudinally therethrough and opening at ends 22a, 24a with a solid, uniform body extending about the central lumen. Other embodiments with a solid, uniform body not including a central lumen or other passage or passages are also contemplated. Body 21a includes a cross-section transversely to longitudinal axis 29a that includes a first bending axis 25a extending through longitudinal axis 29a and transversely to the length of body 21a. Body 21a also includes a second bending axis 26a extending through longitudinal axis 29a transversely to the length of body 21a and orthogonally to first bending axis 25a. The cross-section of body 21a includes an oval shape with the elongated portion of the oval shape extending along first bending axis 25a. This provides a greater moment of inertia and thus a greater resistance to bending than is provided about second bending axis 26a, which extends between the shorter sides of the oval shape. The oval-shaped cross-section can be carried along substantially the entire length of connecting element 20a between first and second ends 22a, 24a.

Connecting element 20a can be engaged by anchors to the vertebral bodies with first bending axis 25a extending along or in the generally same direction as the engagement axis of the anchors. This provides resistance to bending of the spinal motion segment in a plane of motion that includes bending axis 25a. For example, if connecting element 20a were secured to the spinal motion segment in the position shown for connecting element 10 in FIG. 1A, the plane of motion including first bending axis 25a includes extension and flexion of the spinal motion segment, and the plane of motion including second bending axis 26a includes lateral bending of the spinal motion segment. Since connecting element 20a has a moment of inertia that is less in the direction of bending axis 26a than in the direction of bending axis 25a, connecting element 20a can permit more motion of the spinal column segment in lateral bending than in spinal extension flexion.

In another embodiment, connecting element 20b shown in FIG. 1E includes a body 21b extending along longitudinal axis 29b. Body 21b includes an oval shaped cross-section like connecting element 20a, but is oriented so that second bending axis 26b extends along or in the general direction of engagement axis 109. First bending axis 25b is oriented to extend tangentially to or along the vertebral body of the spinal motion segment to which connecting element 20b is attached. Accordingly, if connecting element 20b were engaged posteriorly along the spinal column in the position of connecting element 10 as shown in FIG. 1A, second bending axis 26b would extend in the general direction of engagement axis 109. Engagement axis 25b would extend along vertebral body V1 and provide greater resistance to lateral bending than would be provided about engagement axis 26b with respect to extension and flexion of the spinal motion segment.

Figures 2A, 2B:
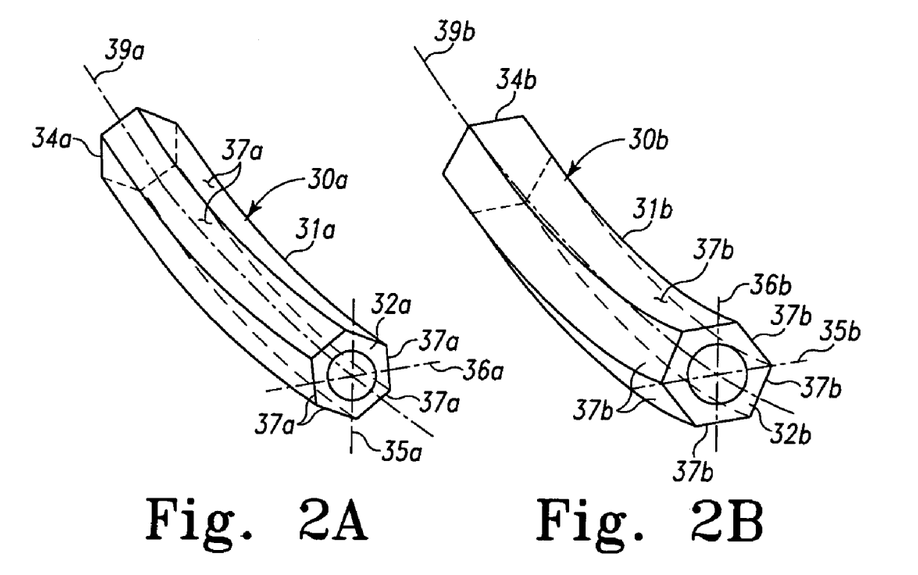
FIGS. 2A and 2B are perspective views of another embodiment connecting element in first and second implantation orientations, respectively.

FIGS. 2A and 2B show another embodiment connecting element in first and second implantation orientations, respectively. Connecting element 30a includes a body 31a having a hexagonally shaped cross-section extending along longitudinal axis 39a between a first end 32a and an opposite second end 34a. Body 31a includes a first bending axis 35a extending through longitudinal axis 39a and opposing vertices of the hexagonal shape, and a second bending axis 36a extending through longitudinal axis 39a and opposing planar surfaces 37a of the hexagonal shape. First and second axes 35a, 36a are orthogonally oriented relative to one another. Since a greater moment of inertia is defined about the first bending axis 35a, a greater resistance is bending is provided with respect to a plane of motion that includes bending axis 35a than a plane of motion that includes bending axis 36a. Connecting element 30a can be secured to the spinal motion segment with first bending axis 35a extending along or in the general direction of engagement axis 109.

In FIG. 2B a similarly shaped connecting element 30b includes a body 31b with a hexagonally shaped cross-section extending along longitudinal axis 39b between first end 32b and second end 34b. Body 31b is oriented so that second bending axis 36b extending through longitudinal axis 39b and opposite planar surfaces 37b is oriented in the direction of engagement axis 109 of the anchor into the vertebral body when secured to the spinal motion segment. First bending axis 35b extending through longitudinal axis 39b and opposing vertices of the cross-section is oriented in the direction tangentially to or along the spinal motion segment, and provides greater resistance to spinal motion in this direction than in the direction in which bending axis 36b extends.

Figures 3A, 3B:
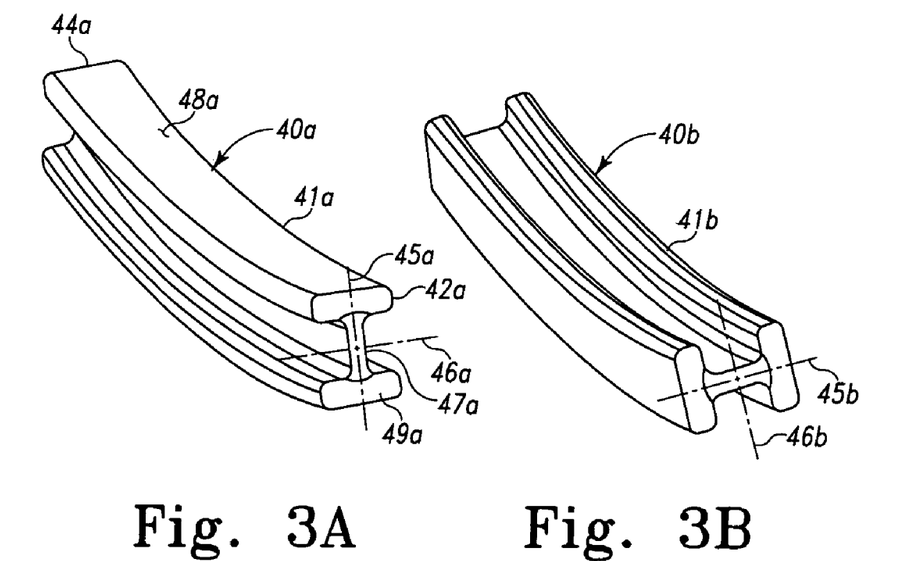
FIGS. 3A and 3B are perspective views of another embodiment connecting element in first and second implantation orientations, respectively.

FIGS. 3A and 3B show another embodiment connecting element in first and second orientations, respectively. Connecting element 40a includes a body 41a having an I-beam shaped cross-section extending between a first end 42a and an opposite second end 44a. Body 41a includes a first bending axis 45a extending along a web 47a of body 41a and through opposing flanges 48a, 49a. A second bending axis 46a extends transversely to web 47a and generally parallel to flanges 48a, 49a. First and second axes 45a, 46a are orthogonally oriented relative to one another. A greater moment of inertia is defined about the first bending axis 45*a* due to the greater height and the area of the flanges, and therefore a greater resistance to bending is provided with respect to a plane of motion that includes bending axis 45*a* than a plane of motion that includes bending axis 46*a*. First bending axis 45*a* can extend in the direction of engagement axis 109 when engaged to the spinal motion segment, and second bending axis 46*a* extends tangentially to or along the vertebral bodies of the spinal motion segment.

In FIG. 3B connecting element 40*b* includes a body 41*b* with an I-beam shaped cross-section like connecting element 40*a*, but body 41*b* is oriented so that second bending axis 46*b* extending parallel to the flanges is oriented in the direction along engagement axis 109 when engaged to the spinal motion segment. First bending axis 45*b* extending along the web is oriented along or tangentially to the vertebral bodies of the spinal motion segment, and provides greater resistance to bending of the spinal motion segment in planes of motion that include bending axis 45*b* than in planes of motion that extend toward the spinal column motion segment along bending axis 46*b*.

Figures 4A, 4B, 5A, 5B:
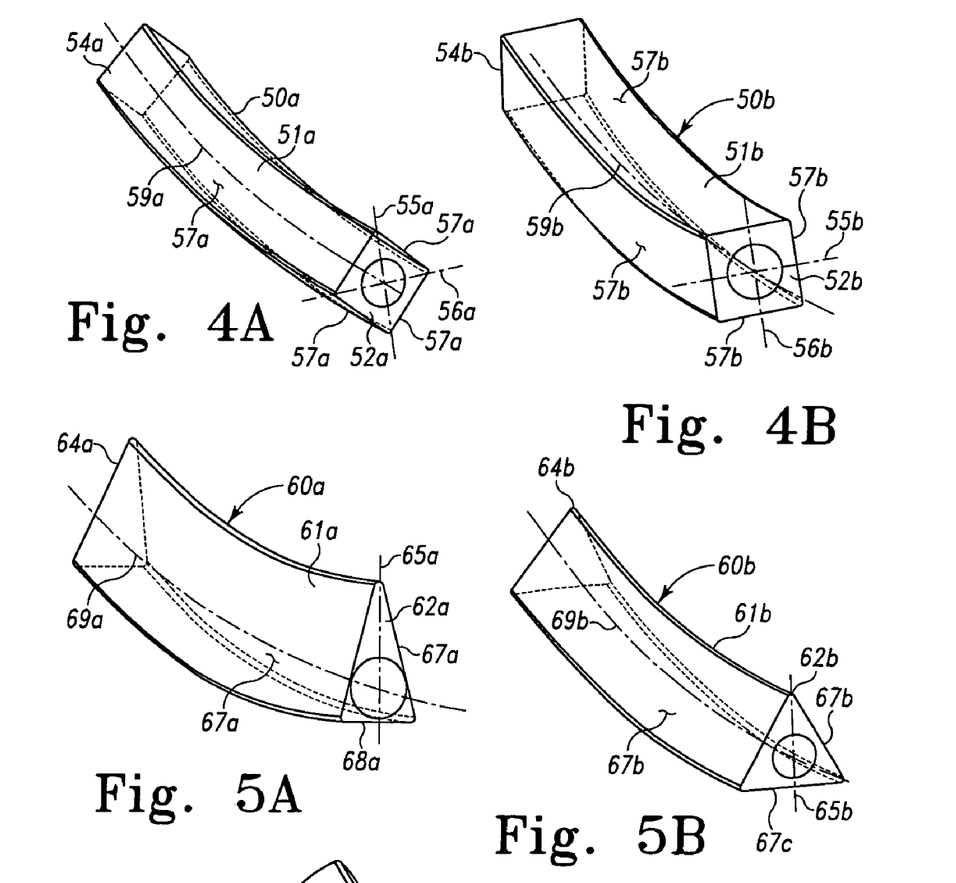
FIGS. 4A and 4B are perspective views of another embodiment connecting element in first and second implantation orientations, respectively.
FIGS. 5A, 5B and 5C are perspective views of additional embodiments of connecting elements in a first implantation orientation.

FIG. 4A shows another embodiment connecting element 50*a*. Connecting element 50*a* includes a body 51*a* having a diamond shaped cross-section extending along longitudinal axis 59*a* between a first end 52*a* and an opposite second end 54*a*. Body 51*a* includes a first bending axis 55*a* extending through opposing vertices of the diamond shape and longitudinal axis 59*a*, and a second bending axis 56*a* extending through the other opposing vertices of the diamond shape and longitudinal axis 59*a*. First and second bending axes 55*a*, 56*a* are orthogonally oriented relative to one another. When implanted, first bending axis 55*a* extends toward the spinal motion segment to which connecting element 50*a* is attached, and second bending axis 56*a* extends along the spinal motion segment. Since the same moment of inertia is defined about the first bending axis 55*a* and second bending axis 56*a*, the same resistance to bending is provided with respect to the plane of motion that includes bending axis 55*a* and the plane of motion that includes bending axis 56*a*. However, the planar side surfaces 57*a* extending between the vertices provide less resistance to bending in planes of motion that include bending axes extending through the planar side surfaces 57*a*. Accordingly, connecting element 50*a* provides a body 51*a* that is less stiff in planes of motion that are obliquely oriented to the planes of motion including bending axes 55*a*, 56*a*.

In FIG. 4B connecting element 50*b* includes a body 51*b* with a square-shaped cross-section that is similar to the diamond-shaped cross-section of FIG. 4A but is rotated 90 degrees about longitudinal axis 59*b* relative to the FIG. 4A orientation. First bending axis 55*b* and second bending axis 56*b* are oriented orthogonally to one another and extend through longitudinal axis 59*b* and the planar sides 57*b* of body 51*b*. Connecting element 50*b* can be secured to the spinal motion segment in an orientation that is rotated 45 degrees about longitudinal axis 59*b* from the orientation shown in FIG. 4A. Since the moment of inertia about the axes 55*b*, 56*b* is less than the moment of inertia about axes 55*a*, 56*a*, connecting element 50*b* provides less stiffness to resist bending forces in plane of motions that includes axes 55*b*, 56*b*. The stiffness increases in axes that are obliquely oriented to bending axes 55*b*, 56*b* to a maximum stiffness about axes that extend through the vertices of the cross-sectional shape.

In FIG. 5A there is shown another embodiment connecting element 60*a* having a body 61*a* defining a triangularly-shaped cross-section extending along longitudinal axis 69*a* between a first end 62*a* and a second end 64*a*. Body 61*a* includes an isosceles triangular shape with a pair of equal, longer sides 67*a* meeting at a first vertex and a shorter side 68*a* extending between long sides 67*a* opposite the first vertex. A first bending axis 65*a* extends through the first vertex, longitudinal axis 69*a* and shorter side 68*a*. Body 61*a* is engageable to vertebral bodies with bending axis 65*a* extending along the engagement axis 209 of the anchors toward the spinal motion segment to which connecting element 60*a* is attached. A greater moment of inertia is provided about first bending axis 65*a* that in directions about axes that are transversely oriented to bending axis 65*a*.

Other embodiments contemplate other triangular arrangements for the cross-sectional shape of the connecting element. For example, FIG. 5B shows a connecting element 60*b* having a body 61*b* with an equilateral triangular arrangement along longitudinal axis 69*b* between first end 62*b* and second end 64*b*. Body 61*b* includes side surfaces 67*b* having an equal length between vertices about longitudinal axis 69*b*. A first bending axis 65*b* extends through a vertex of body 61*b*, longitudinal axis 69*b*, and through the opposite side surface 67*b*. Bending axis 65*b* can extend along or in the direction of the engagement axis 109 of the anchor and toward the spinal motion segment to which connecting element 65*b* is attached.

Figure 5C:
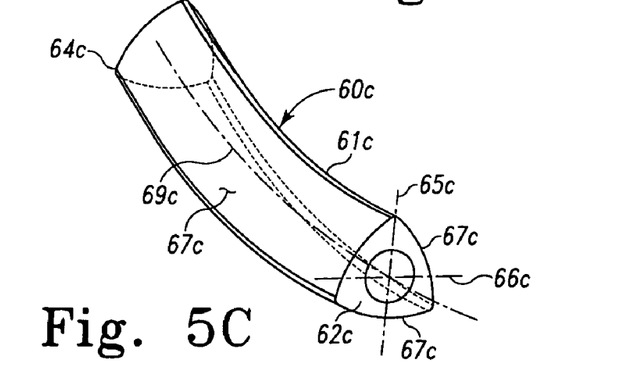

In FIG. 5C, there is shown another embodiment connecting element 60*c* having a body 61*c* with a triangular shaped cross-section along longitudinal axis 69*c*. Body 61*c* has convexly curved side surfaces 67*c* extending between vertices of the triangular shape. A bending axis 65*c* extends through one of the vertices and through the opposite convexly curved side surface 67*c* toward the spinal motion segment to which connecting element 60*c* is attached. Still other embodiments contemplate other triangular shapes, including scalene triangular shapes, isosceles triangular shapes with a pair of equal short sides and a longer side extending between the shorter sides, and triangular shapes with concavely surface wall surfaces extending about the cross-section of the body.

Other embodiments having other cross-sectional shapes extending along the longitudinal axis of the connecting element are also contemplated. For example, in FIG. 6A, connecting element 70*a* is shown with an elongated body 71*a* having an oblong or race-track shaped cross-section extending between first and second ends 72*a*, 74*a*. Body 71*a* has a first bending axis 75*a* defining a first moment of inertia thereabout that is greater than a moment of inertia about a second bending axis 76*a* extending orthogonally to first bending axis 75*a*. First bending axis 75*a* extends in the direction of the oblong or elongated side surfaces 77*a* of the cross-section of body 71*a* and along the anchor engagement axis toward the spinal motion segment when attached thereto. Second bending axis 76*a* extends in the shorter direction of the cross-section of body 71*a* transversely to side surfaces 77*a* and along the adjacent vertebral body when attached thereto. Connecting element 70*a* can be secured to the spinal motion segment with first bending axis 75*a* extending in the direction of engagement axis 109 of the anchors.

Figure 6A:
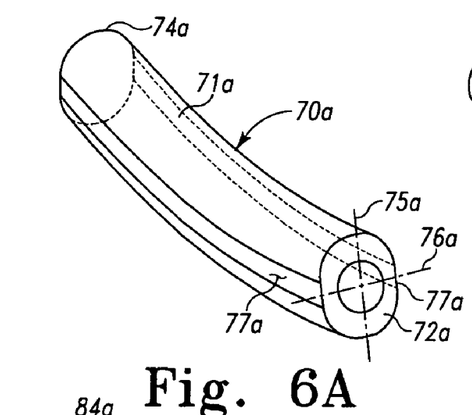
FIGS. 6A and 6B are perspective views of another embodiment connecting element in first and second implantation orientations, respectively.
Figure 6B:
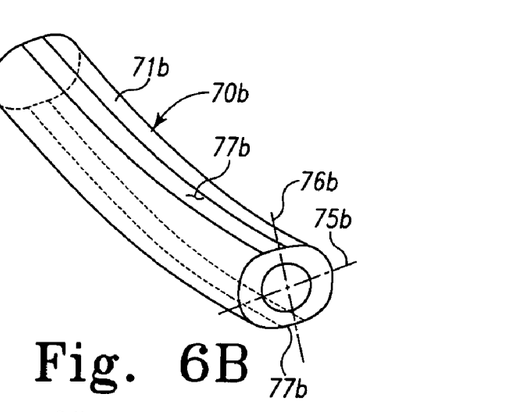

In FIG. 6B, connecting element 70*b* includes a body 71*b* that with a cross-sectional shape that is similar in shape to body 71*a*, but is rotated 90 degrees about its longitudinal axis relative to the FIG. 6A orientation. Body 71*b* includes a first bending axis 75*b* and a second bending axis 76*b* that are oriented to extend orthogonally to their respective orientations in FIG. 6A. Second bending axis 75*b* extends generally along the engagement axis 109 of the anchor and toward the spinal motion segment when attached thereto, and first bending axis 75*b* extends along the adjacent vertebral body when attached thereto.

Figure 7A:
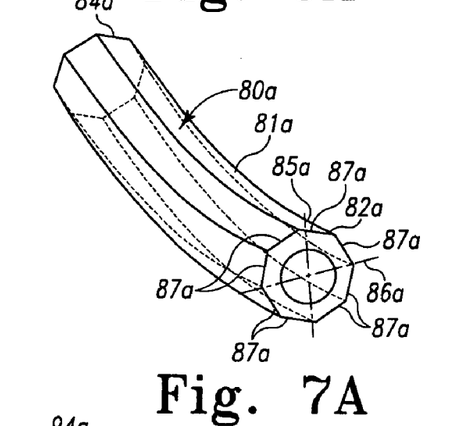
FIGS. 7A and 7B are perspective views of another embodiment connecting element in first and second implantation orientations, respectively.

In another example, in FIG. 7A, connecting element 80*a* is shown with an elongated body 81*a* having an octagonal shaped cross-section extending between first and second ends 82a, 84a. Body 81a has a first bending axis 85a defining a first moment of inertia thereabout that is the same as a moment of inertia about a second bending axis 86a extending orthogonally to first bending axis 85a. First bending axis 85a extends through opposite vertices of the octagonal shape, and second bending axis 86a extends orthogonally to first bending axis 85a and through opposite vertices of the octagonal shape. Accordingly, the moment of inertia about each of the bending axes 85a, 86a is the same. The opposite planar wall surfaces 87a between adjacent vertices have a height therebetween that is less than the height between opposite vertices, and thus provide a lesser moment of inertia and less resistance to motion in planes including axes extending through these opposite planar wall surfaces 87a.

Figure 7B:
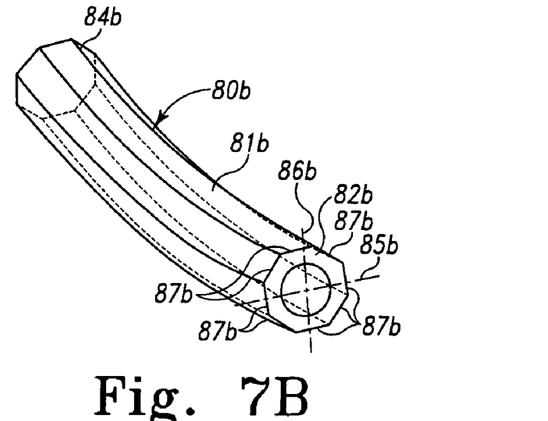

In FIG. 7B, connecting element 80b includes a cross-sectional shape that is similar to connecting element 80a, but the cross-sectional shape of body 81b is rotated about its longitudinal axis relative to the orientation of body 81a shown in FIG. 7A. Body 81b extends between first and second ends 82b, 84b, and includes first and second bending axes 85b, 86b extending through opposite planar wall surfaces 87b of the octagonal shape. Accordingly, the moment of inertia about these bending axes is the same; however, axes extending through opposite vertices of the octagonal shape have a greater moment of inertia and provide a greater resistance to bending in planes of motion including these axes.

Figure 8A:
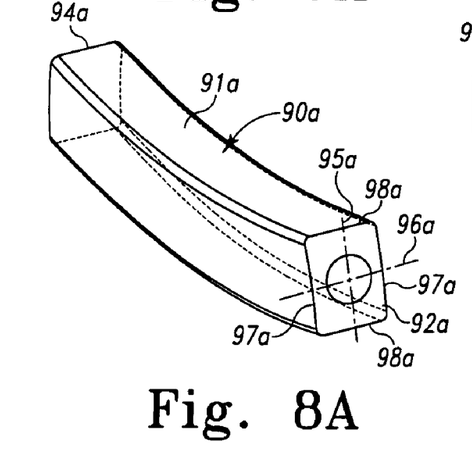
FIGS. 8A and 8B are perspective views of another embodiment connecting element in first and second implantation orientations, respectively.

In FIG. 8A, connecting element 90a is shown with an elongated body 91a having a rectangular shaped cross-section extending between first and second ends 92a, 94a. Body 91a has a first bending axis 95a extending in the direction of elongated side surfaces 97a of the cross-section of body 91a, and a second bending axis 96a extending in the direction of the shorter side surfaces 98a of the cross-section of body 91a. Body 91a this has first bending axis 95a defining a first moment of inertia thereabout that is greater than a moment of inertia about second bending axis 96a extending orthogonally to first bending axis 95a. Connecting element 90a can be secured to the spinal motion segment with first bending axis 95a extending in the direction of the anchor engagement axis 109 toward the vertebral body to which connecting element 90a is to be attached.

Figure 8B:
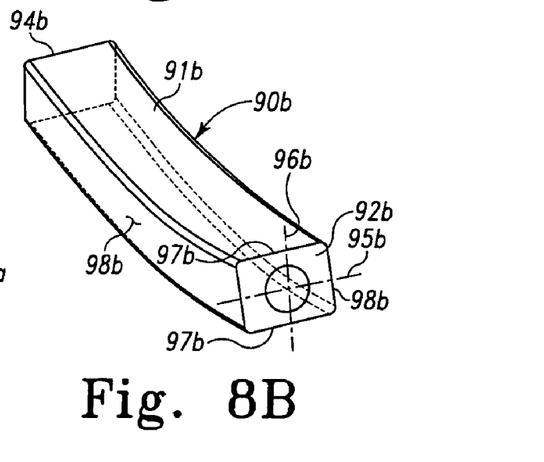

In FIG. 8B, connecting element 90b includes a body 91b with a cross-sectional shape that is similar to body 91a in FIG. 8A. However, the cross-sectional shape of body 91b is rotated 90 degrees about its longitudinal axis relative to the orientation of body 91a shown in FIG. 8A. Body 91b includes a second bending axis 96b extending parallel to the shorter side surfaces 98b, and is oriented to extend along the anchor engagement axis 109 toward the spinal motion segment when connecting element 90b is attached thereto. First bending axis 95b is orthogonally oriented to second bending axis 96b, and extends generally parallel to the longer side surfaces 98b.

Figure 9:
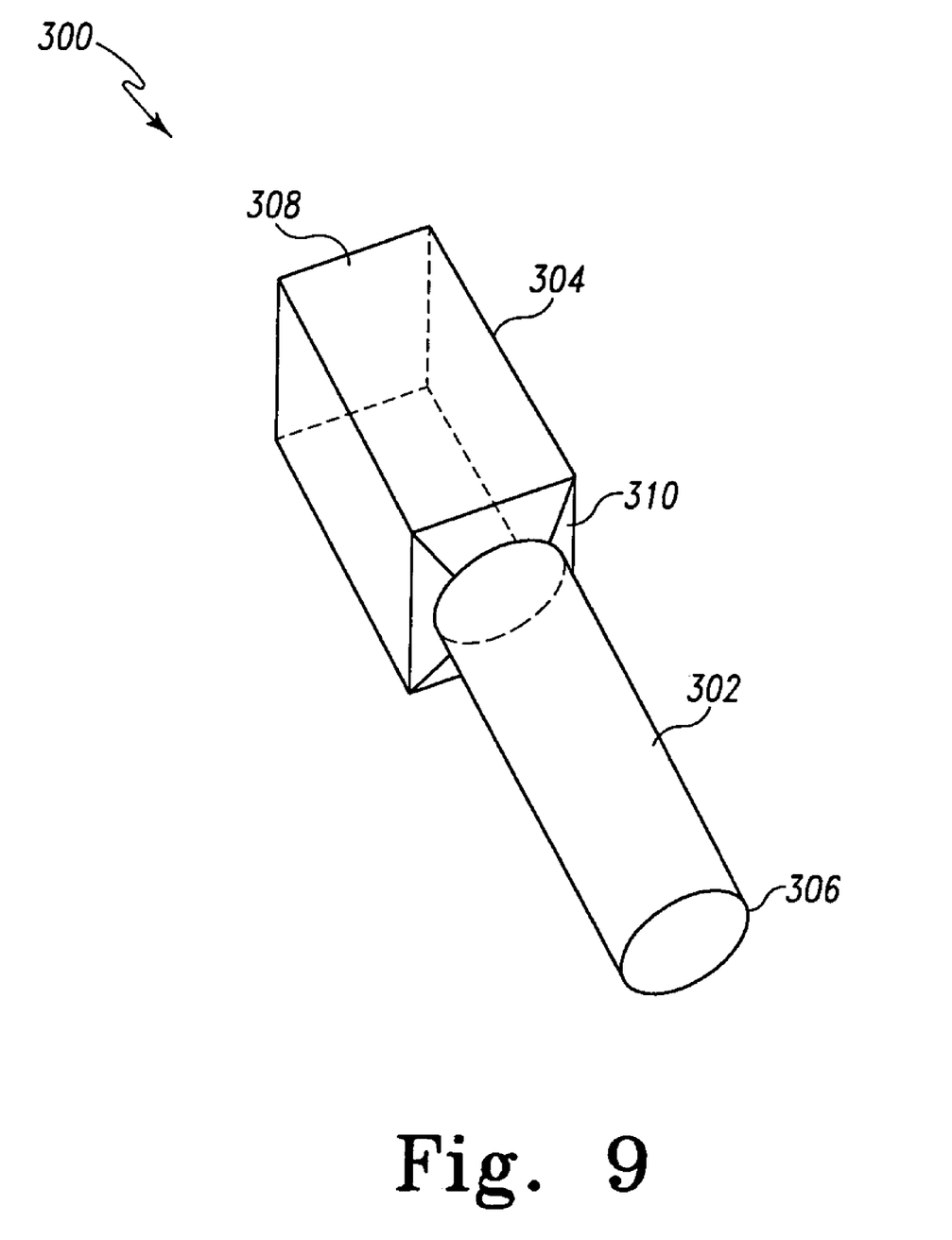
FIG. 9 is a perspective view of another embodiment connecting element.

In FIG. 9, another embodiment connecting element 300 is shown having a first portion 302 with a first cross-sectional shape and a second portion 304 with a second cross-sectional shape. First portion 302 can be joined to second portion 304 at a transition region 310. First portion 302 extends from transition region 310 to a first end 306, and second portion 304 extends from transition region 310 to a second end 308. In the illustrated embodiment, first portion 302 includes an oval cross-sectional shape along the length thereof, and second portion 304 includes a rectangular cross-sectional shape on the length thereof. It is contemplated that any combination of two or more cross-sectional shapes discussed herein could be formed as a single integral connecting element with transition regions therebetween.

The respective portions 302, 304 of connecting element 300 can have a length each sized to extend between vertebrae of a spinal motion segment so that connecting element 300 can be engaged to three or more vertebrae. Other embodiments contemplate that the portions have a length extending from the transition regions sized to span approximately one half the distance between vertebrae of a spinal motion segment.

Figures 10, 11A, 11B, 11C:
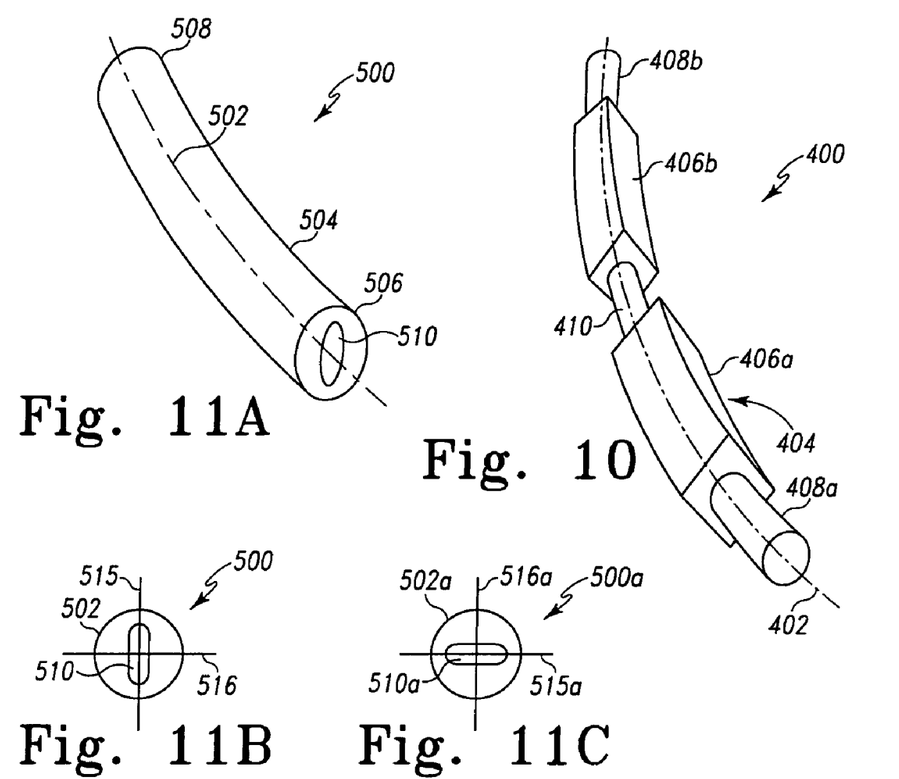
FIG. 10 is a perspective view of another embodiment connecting element.
FIG. 11A is a perspective view of another embodiment connecting element.
FIGS. 11B-11G are various embodiments of cross-sections for connecting elements.

Referring to FIG. 10, there is shown another embodiment connecting element 400 including an elongated body 404 extending along a longitudinal axis 402. Body 404 includes a number of stabilization portions 406a, 406b along its length having non-circular cross-sectional shapes orthogonally to longitudinal axis 402. Any one or combination of the non-circular cross-sectional shapes discussed herein can be provided along one or both of the stabilization portions 406a, 406b. Stabilization portions 406a, 406b can be connected to one another with one or more intermediate connecting portions 410 having a circular cross-sectional shape orthogonal to longitudinal axis 402. In addition to or alternatively to intermediate connecting portion or portions 410, connecting element 400 includes end connecting portions 408a, 408b having a circular cross-sectional shape orthogonal to longitudinal axis 402.

End connecting portions 408a, 408b and/or intermediate connecting portion 402 can be located for engagement with anchors to secure connecting element 400 along the spinal column. The circular cross-section regions can provide an engagement platform for anchoring systems typically employed to engage spinal rods of circular cross-section along the spinal column, while providing the controlled bending characteristics between the anchors with stabilization portions 406a, 406b.

Referring now to FIG. 11A, there shown a connecting element 500 having an elongated body 504 extending along a longitudinal axis 502 between a first end 506 and a second end 508. Body 504 includes a circular cross-section orthogonally to longitudinal axis 502. Body 504 also includes a lumen 510 extending therethrough and along a length thereof about longitudinal axis 502. Lumen 510 includes a non-circular cross-sectional shape so that the cross-section of body 504 is anisotropic along longitudinal axis 502.

For example, in FIG. 11B lumen 510 includes an oval shaped cross-section with an elongate portion of the oval extending along first bending axis 515 and shorter portion of the lumen extending along a second bending axis 516. The moment of inertia about first bending axis 515 is less than the moment of inertia about second bending axis 516, and thus connecting element 500 is less resistant to bending forces about bending axis 515 than bending axis 516. When implanted, first bending axis 515 can extend generally in the direction of engagement axis 109 and toward the spinal motion segment to which connecting element 500 is to be attached.

In FIG. 11C, connecting element 500a includes body 502a rotated 90 degrees from its orientation in FIG. 11B. Body 502a includes lumen 510a elongated such that first bending axis 516a extends between the shorter sides of the oval shape and second bending axis 515a extends in the elongated direction of the oval shape. First bending axis 516a can be oriented in the direction along engagement axis 109 toward the spinal motion segment to which connecting element 500a is to be engaged.

Figure 11D:
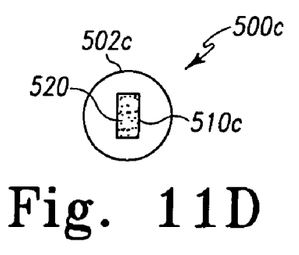
Figure 11E:
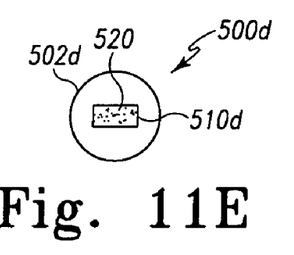

FIGS. 11D and 11E show other embodiment connecting elements 500c and 500d similar to connecting element 500 discussed above. Connecting element 500c includes a body 502c defining a rectangular lumen 510c in a first orientation, and in FIG. 11E connecting element 500d includes a body 502d defining a rectangular lumen 510d oriented 90 degrees from the FIG. 11D orientation. The elongated shape of the rectangular lumen 510c, 510d can be positioned relative to the spinal column to so that the bending axis providing a desired stabilization effect and resistance to bending loads is oriented along the engagement axis toward the spinal column segment.

Figure 11F:
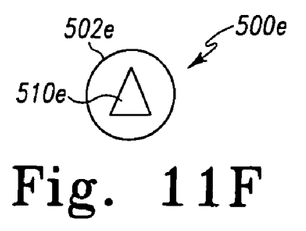
Figure 11G:
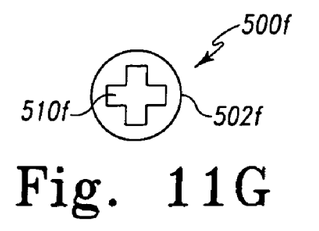

In FIG. 11F, connecting element 500e includes a body 502e defining a lumen 510e with a triangularly shaped cross-section extending therealong. In FIG. 11G, connecting element 500f includes a body 502f defining a lumen 510f defining a cross shaped cross-section. Again, the connecting elements 500e, 500f can be oriented in the desired position relative to the spinal column segment to provide a desired stabilization effect.

It is further contemplated that the non-circular lumens can include biodegradable material 520, such as shown in FIGS. 11D and 11E, to provide an initial stiffness upon implantation a lesser stiffness over time. The biodegradable material can provide rigidity and support for both the connecting element and, consequently, the attached bone structures. In use, the biomechanical load supported by the composite material and connecting element incorporating the composite can vary over time. This allows the orthopedic device to become dynamizable, or change its physical properties in vivo.

As material 520 biodegrades, the rigidity of connecting element 500 decreases. This decrease in rigidity can be substantially linear over time. The nature and composition of material 520 can be varied to allow material 520 to degrade over varying time periods including periods between a few days, a few weeks, a few months, and even over the course of one or more years.

The biodegradable material can include polymeric materials formed from oligomers, homopolymers, copolymers, and polymer blends that include polymerized monomers derived from l, d, or d/l lactide (lactic acid); glycolide (glycolic acid); ethers; amino acids; anhydrides; orthoesters; hydroxy esters; and mixtures of these monomeric repeating units. Use of the term "copolymers" is intended to include within the scope of the invention polymers formed of two or more unique monomeric repeating units. Such copolymers can include random copolymers; graft copolymers; body copolymers; radial body, dibody, and tribody copolymers; alternating copolymers; and periodic copolymers. Use of the term "polymer blend" is intended to include polymer alloys, semi-interpenetrating polymer networks (SIPN), and interpenetrating polymer networks (IPN).

In one embodiment, the biodegradable material comprises a biodegradable polymeric material including: poly(amino acids), polyanhydrides, polycaprolactones, poly(lactic-glycolic acid), polyhydroxybutyrates, polyorthoesters, and poly (d,l-lactide). In other embodiments, the biodegradable material can comprise biodegradable ceramic materials and ceramic cements. Examples of biodegradable ceramic materials include: hydroxyapatite, hydroxyapatite carbonate, corraline, calcium phosphate, tricalcium phosphatem, and hydroxy-apatate particles. Examples of biodegradable ceramic cements include calcium phosphate cement.

In still other embodiments, the biodegradable material can be formed of composite materials. Examples of composite materials include as a base material or matrix, without limitation: ceramics, resorbable cements, and/or biodegradable polymers listed above. Each of the base materials can be impregnated or interspersed with fibers, platelets, and particulate reinforcing materials. In one form, the biodegradable material comprises a resorbable, moldable material that can be molded at an elevated temperature and then allowed to set up into a hardened material at around body temperature, such as the material sold under the trade name BIOGLASS®.

Further, the biodegradable material can be formulated to degrade or can be induced to begin degradation by application of external stimuli. For example, the biodegradable material can degrade upon application of radiation such as UV radiation, thermal energy, and/or solvent-either neutral, basic, or acidic.

The portion of connecting element 500 about lumen 506, or the material of any of the connecting element embodiments discussed herein, can be comprised of nonbiodegradable or biostable material. Such material can include resilient materials such as, without limitation, nitinol, titanium, titanium-vanadium-aluminum alloy, cobalt-chromium alloy, cobalt-chromium-molybdenum alloy, cobalt-nickel-chromium-molybdenu-m alloy, biocompatible stainless steel, tantalum, niobium, hafnium, tungsten, and alloys thereof; polymeric materials include polymerized monomers derived from: olefins, such as ethylene, propylene, butene-1, pentene-1, hexene-1, 4-methylpentene-1, styrene, norbornene and the like; butadiene; polyfunctional monomers such as acrylate, methacrylate, methyl methacrylate; esters, for example, caprolactone and hydroxy esters; and mixtures of these monomeric repeating units. Particular polymers include carbon poly (ether, ether, ketone) (PEEK), poly(aryl ether, ketone) (PAEK), and the like.

In the embodiments discussed above, the connecting elements can be curved along their respective longitudinal axes. One of the bending axes can extend between the convexly curved and concavely curved portions of the body. As discussed further below, the curved bodies can facilitate placement of the connecting element into the body of the patient along a minimally invasive insertion path where a selected bending axis extending between the convexly and concavely curved sides of the connecting element is oriented toward the vertebral bodies in the general direction of engagement axis 109. The selected bending axis can be engaged to the first and second anchors to extend in the direction of the engagement axes of the anchors engaged to the vertebral bodies. It is also contemplated that the connecting elements can be linear or include compound curvature. The connecting elements can be made from metal or metal alloy, plastics, polymers, or other suitable biocompatible material.

Figure 12:
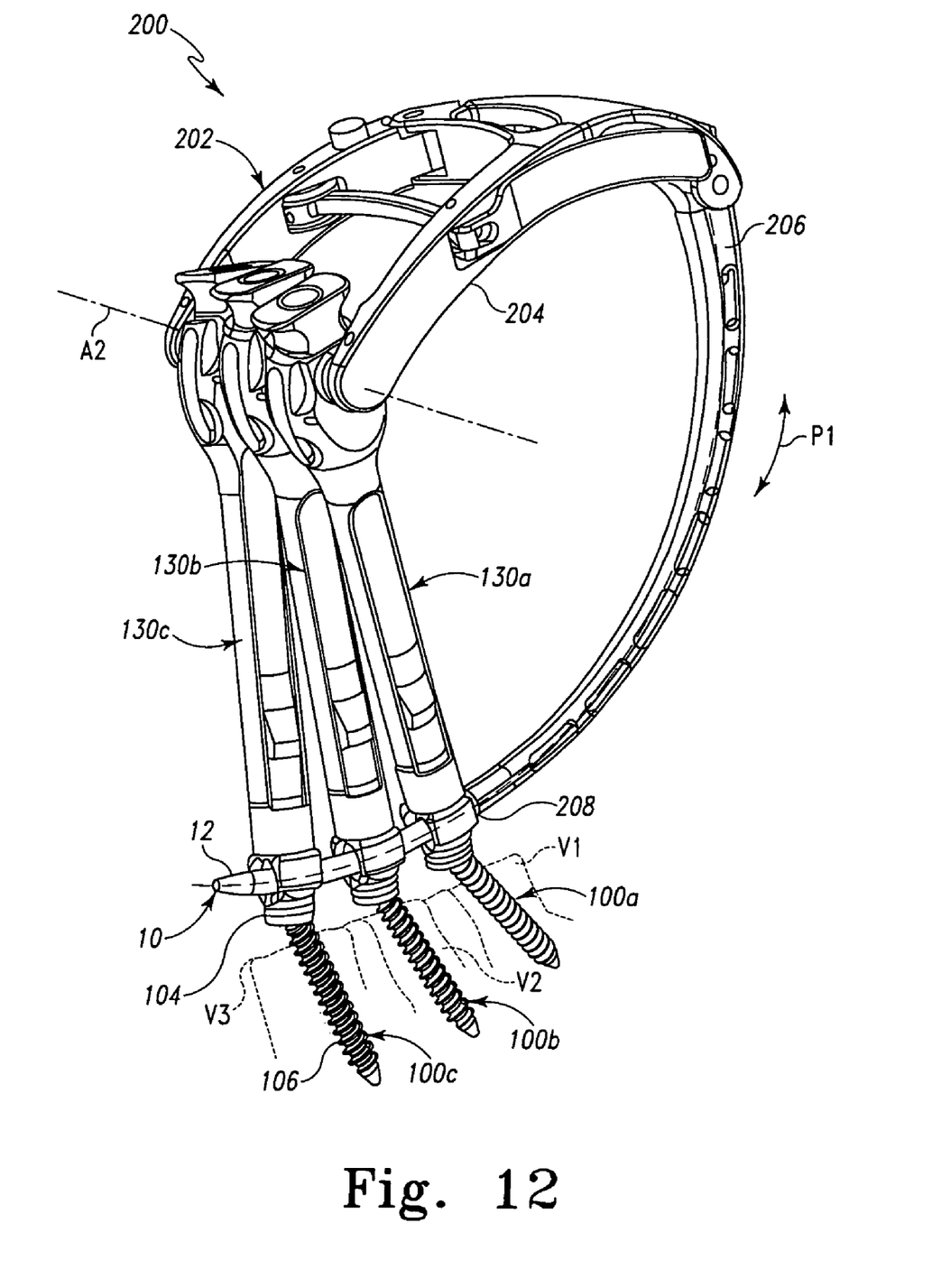
FIG. 12 shows one embodiment of a system for positioning a connecting element in a predetermined orientation along the spinal column in a minimally invasive surgical procedure.

Various instruments and systems are contemplated for positioning the connecting elements into the patient in minimally invasive surgical techniques while maintaining a desired orientation of the connecting element relative to the spinal motion segment or segments to which it is to be attached. In FIG. 12 there is shown an inserter instrument 200 including an inserter 202 pivotally mounted to a number of anchors extensions 130a, 130b, 130c. Inserter 202 includes a mounting portion 204 and a pivot arm 206 extending from mounting portion 204. Connecting element 10 includes a trailing end that is releasably engaged to the distal end 208 of pivot arm 206. Connecting element 10 can include any form discussed herein in which the stiffness about a first bending axis differs than a stiffness about a second bending axis that is transversely oriented to the first bending axis. Connecting element 10 may include a leading end 12 that is tapered to facilitate placement through tissue of the patient, although such is not required.

Inserter instrument 200 further includes anchor extensions 130a, 130b, 130c (collectively and individually referred to as extension or extensions 130) releasably mounted to respective ones of anchors 100a, 100b, 100c (collectively and individually referred to as anchor or anchors 100). Anchors 100 includes bone engaging portion 106 engageable to respective ones of vertebrae V1, V2, V3, and a proximal receiver 104 for receiving connecting element 10 therein. A set screw or other engaging member (not shown) can be delivered through the extensions 130 to engage the connecting element in the respective receiver 104. Receiver 104 can be pivotal relative to bone engaging portion 106 so that bone engaging portion 106 and receiver 104 include a multi-axial arrangement therebetween. In another embodiment, receiver 104 can be fixed relative to bone engaging portion 106.

Anchors 100 and anchor extensions 130 can be engaged to the respective vertebrae through one or more percutaneous access portals that minimize incision length and tissue retraction. The anchor extensions 130 can include an elongated body extending between a distal end mounted to the receivers of the anchors and a proximal end spaced proximally from the anchors. Inserter 202 is pivotally mounted to the proximal ends of extensions 130, and movable relative thereto about pivot axis A2 to swing pivot arm 206 and thus connecting element 10 along an arcuate insertion path P1. Accordingly, connecting element 10 can be curved along its length to facilitate placement along path P1, although a curved connecting element is not required.

Connecting element 10 can be mounted to pivot arm 206 so that its respective bending axes are aligned in a predetermined orientation relative to the spinal motion segments defined by vertebrae V1, V2, V3 to provide the desired stabilization effect. Connecting element 10 can be guided in the predetermined orientation from a location remote from anchors 100 through skin and/or tissue of the patient to a location where connecting element 10 extends between the receivers of anchors 100. Connecting element 10 can be engaged in the receivers of the anchors in the predetermined orientation to provide the desired stabilization effect to the spinal motion segment.

Examples of systems, instruments and techniques for minimally invasive placement of connecting elements using inserter instruments mounted to anchor extensions can be discerned from U.S. Pat. No. 6,530,929 to Justis et al, U.S. Patent Application Publication Nos. 2005/0171540 to Lim et al. and 2002/0161368 to Foley et al., and U.S. patent application Ser. No. 11/213,473 filed on Aug. 26, 2005, all of which are incorporated herein by reference in their entirety.

Figure 13:
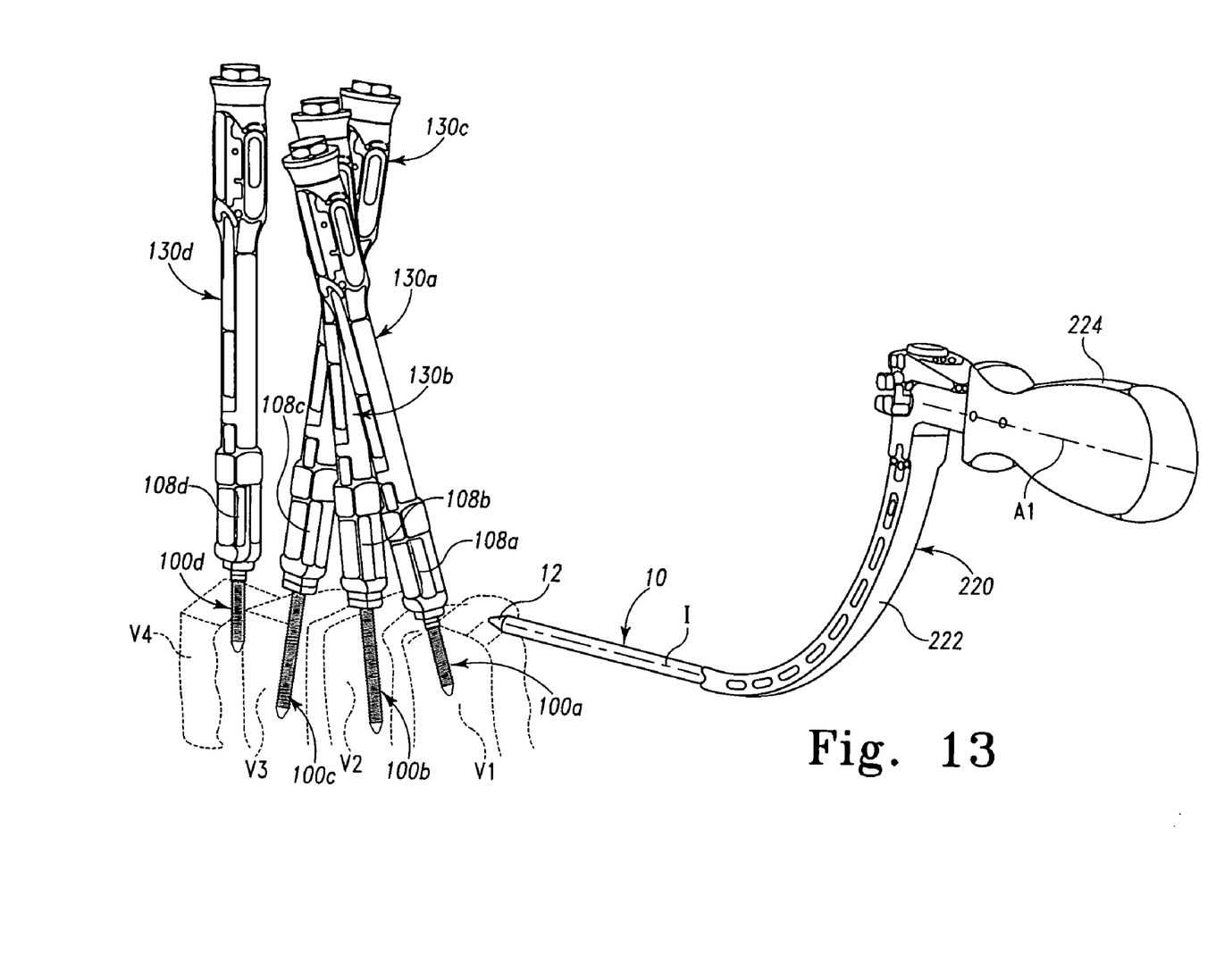
FIG. 13 shows another embodiment system for positioning a connecting element in a predetermined orientation along the spinal column in a minimally invasive surgical procedure.

FIG. 13 shows another embodiment inserter instrument and stabilization system that includes an inserter instrument 220 coupled to connecting element 10. A number of anchors 100a, 100b, 100c, 100d are engaged to a corresponding number of and respective ones of vertebrae V1, V2, V3, V4. Anchor extensions 130a, 130b, 130c, 130d are releasably engaged to and extend proximally from respective ones of the anchors 100a, 100b, 100c, 100d. A receiving space 108a, 108b, 108c 108d is defined between each of the respective anchors 100 and anchor extensions 130.

Inserter instrument 220 includes a curved arm 222 having connecting element 10 releasably engaged to a distal end thereof and a handle 224 extending from a proximal end thereof. Handle 224 can extend along an axis A1 in a generally parallel relation to an axis I along which connecting element 10 extends, although non-parallel arrangements between the handle and connecting element are also contemplated. Connecting element 10 can be coupled to inserter instrument 220 in a predetermined orientation and maintained in the predetermined orientation during insertion so that bending axes of connecting element 10 having differing moments of inertia thereabout are positioned in the desired orientation relative to the spinal motion segments to which connecting element 10 is to be engaged. Connecting element 10 can be percutaneously guided in the predetermined orientation into the patient using free-hand techniques, image guided visualization, and/or surgical navigation systems with inserter instrument 220 to locate connecting element 10 into the receiving spaces 108, and so that connecting element 10 extends between the anchors 100. For connecting element embodiments including a central lumen, the connecting element can be guided along a guidewire, suture or other guiding structure to a location adjacent the anchors.

Anchor extensions 130 can include a member that is movable toward the respective anchor 100 engaged thereto to contact the connecting element 10 in space 108 and seat it into the receivers of the anchors 100. Other embodiments contemplate that reduction instruments can be employed through or beside anchor extensions 130 to seat the connecting element in the anchors 100. Set screws or other engaging members can be delivered through the extensions 130 to secure the connecting element 10 in the receivers of anchors 100 with the bending axes of connecting element 10 in the desired orientations relative to the spinal motion segments. Further examples of inserter 220 and embodiments of anchor extensions 130 are provided in U.S. patent application Ser. No. 11/348,999, filed on Feb. 7, 2006, which is incorporated herein by reference in its entirety.

Figure 14:
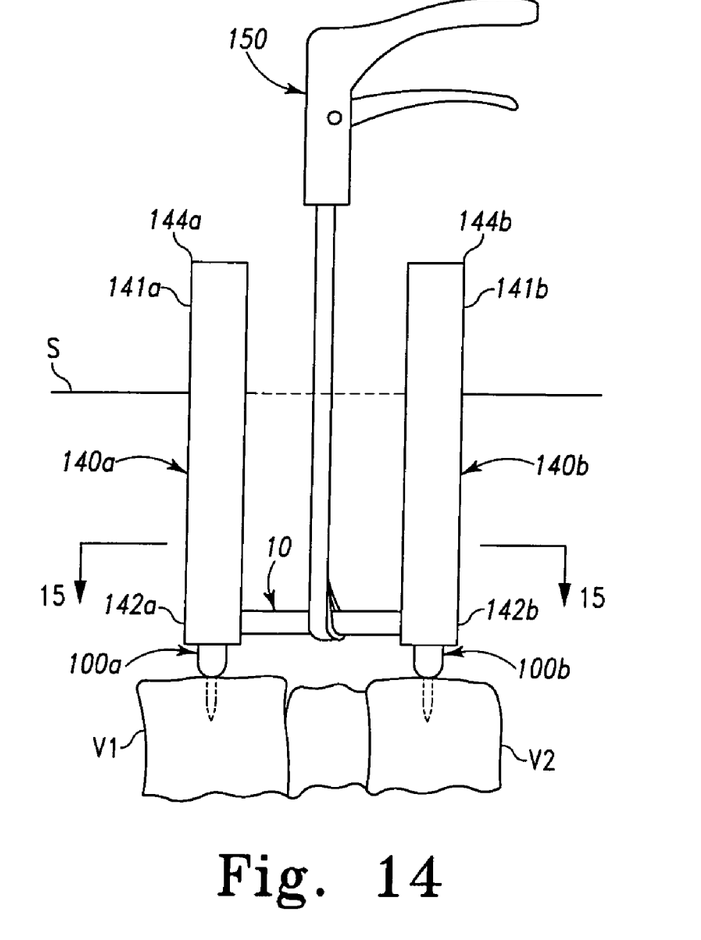
FIG. 14 shows another embodiment system for positioning a connecting element in a predetermined orientation along the spinal column in a minimally invasive surgical procedure.
Figure 15:
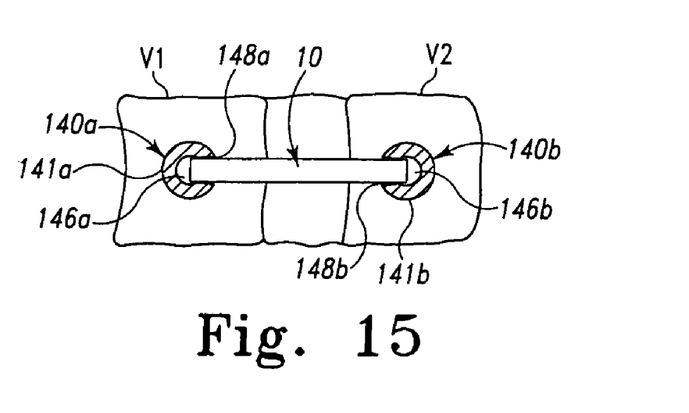
FIG. 15 is a view of the system of FIG. 14 looking in the direction of arrows 15-15.

In FIG. 14, another embodiment system is shown in which anchor extensions 140a, 140b (collectively and individually referred to as anchor extensions 140) are releasably engaged to respective ones of anchors 100a, 100b. Anchor extensions 140 include an elongated, sleeve-like body 141a, 141b with a distal end 142a, 142b mounted to the respective anchor 100 and a proximal end 144a, 144b positioned outside the incision and proximally of skin S of the patient. A passage 146a, 146b extends through body 141a, 141b (FIG. 15).

Connecting element 10 can be guided in a predetermined orientation relative to the spinal motion segments along at least one of the extensions 140 from a location remote from anchors 100 to a location adjacent to anchors 100. In one form, at least one of the anchor extensions 140a, 140b includes an elongated, side-opening slot 148a, 148b oriented toward the other anchor extension. Slots 148a, 148b can extend from distal end 142 of the respective extension 140 toward the proximal end 144. Connecting element 10 can extend through the at least one slot 148 and between extensions 140a, 140b. Connecting element 10 can be grasped by a forceps-like or other suitable inserter instrument 150 and guided along at least one of the extensions 140 to the anchors 100. Contact between connecting element 10 and extensions 140 can maintain connecting element 10 in the predetermined orientation as it is guided to the anchors in a minimally invasive manner. Once connecting element 10 is adjacent to anchors 100, it can be secured to anchors 100 in the predetermined orientation with set screws or other engaging members delivered through extensions 140.

In another embodiment, connecting element 10 is positioned in an end-wise manner into one of the extensions 140 and maneuvered axially therethrough to a distal, side-opening slot 148 of the extension. The leading end of connecting element 10 is then moved out of the slot 148 toward the other anchor extension 140 as its trailing end is further displaced distally in the anchor extension until the connecting element extends between anchors 100 in a cross-wise fashion relative to anchor extensions 140.

In addition to minimally invasive surgical techniques, the connecting elements can be engaged along one or more spinal motion segments in open, invasive surgical procedures where skin and tissue are retracted to expose the implantation location. It is also contemplated that one or more other connecting elements can be engaged to the spinal column along the same vertebral level or levels, or along other vertebral levels. Other procedures can also be completed in conjunction with the stabilization procedure, including discectomy, interbody fusion, artificial disc replacement, bone removal, tissue removal, intravertebral reduction, joint replacement, annular repair, and/or any other spinal surgical procedures.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A system for spinal stabilization, comprising:
a first anchor engageable to a first vertebral body, wherein said first anchor includes a bone engaging portion for engaging the first vertebral body along a first engagement axis;
a second anchor engageable to a second vertebral body, wherein said second anchor includes a bone engaging portion for engaging the second vertebral body along a second engagement axis; and
a connecting element including an elongated body extending between opposite first and second ends and being positionable between and engageable to each of said first and second anchors, wherein said elongated body includes an anisotropic cross-sectional shape defining a first bending axis and a second bending axis transversely oriented to said first bending axis, said body including a first moment of inertia about said first bending axis and a second moment of inertia about said second bending axis that differs from said first moment of inertia, wherein a selected one of said first and second bending axes is aligned in the direction of said first and second engagement axes and said connecting element is engaged to said first and second anchors in said aligned orientation.

2. The system of claim 1, wherein said second bending axis is orthogonal to said first bending axis.

3. The system of claim 1, wherein said connecting element is solid.

4. The system of claim 1, wherein said connecting element includes an elongated lumen extending therealong, said lumen opening at said first and second ends of said elongated body.

5. The system of claim 1, wherein said first and second anchors each include a threaded shaft engageable to the respective first and second vertebral bodies and a receiver at a proximal end of said threaded shaft for receiving the connecting element therein.

6. The system of claim 5, wherein said receiver is pivotal relative to said threaded shaft.

7. The system of claim 1, wherein said anisotropic cross-sectional shape of said connecting element includes a shape selected from the group consisting of: an oval shape, a square shape, a diamond shape, a rectangular shape, a triangular shape, a hexagonal shape, and an octagonal shape.

8. The system of claim 1, wherein said anisotropic cross-sectional shape includes a triangular shape having convexly curved side surfaces extending between vertices of the triangular shape.

9. The system of claim 1, wherein said anisotropic cross-sectional shape includes an I-beam shape with opposite flanges and a central web extending between said flanges.

10. The system of claim 1, wherein:
said connecting element includes a first portion engageable to said first anchor, a second portion engageable to said second anchor, and a transition portion extending between said first and second portions; and
said first portion having a first non-circular cross-sectional shape and said second portion having a second non-circular cross-sectional shape that is different than said first non-circular cross-sectional shape.

11. The system of claim 1, wherein said first moment of inertia is greater than said second moment of inertia.

12. The system of claim 1, wherein said first moment of inertia is less than said second moment of inertia.

13. The system of claim 1, wherein said elongated body is curved along a length thereof between said first and second ends.

14. The system of claim 1, wherein said anisotropic cross-sectional shape is uniform between said first and second ends of said elongated body.

15. A system for spinal stabilization, comprising:
a first anchor engageable to a first vertebral body, wherein said first anchor includes a bone engaging portion for engaging the first vertebral body along a first engagement axis;
a second anchor engageable to a second vertebral body, wherein said second anchor includes a bone engaging portion for engaging the second vertebral body along a second engagement axis;
a first anchor extension including a distal end releasably engageable to said first anchor, said first anchor extension including an elongated body extending proximally from said distal end to a proximal end;
a second anchor extension including a distal end releasably engageable to said second anchor, said second anchor extension including an elongated body extending proximally from said distal end to a proximal end;
an inserter instrument; and
a connecting element including an elongated body positionable between and engageable to each of said first and second anchors, wherein said elongated body includes an anisotropic cross-sectional shape defining a first bending axis and a second bending axis transversely oriented to said first bending axis, said body including a first moment of inertia about said first bending axis and a second moment of inertia about said second bending axis that differs from said first moment of inertia, wherein said inserter instrument is engaged with said connecting element with a selected one of said first and second bending axes in a predetermined orientation relative to said first and second engagement axes of said first and second anchors, and said inserter instrument is operable to move said connecting element while maintaining said predetermined orientation from a location remote from said first and second anchors to a location adjacent said first and second anchors for engagement of said connecting element to said first and second anchors in said predetermined orientation.

16. The system of claim 15, wherein said inserter instrument includes a mounting portion pivotally mounted to said proximal ends of said anchor extensions and an inserter arm extending from said mounting portion along an arc, said connecting element being releasably engaged to a distal end of said inserter arm.

17. The system of claim 16, wherein said elongated body of said connecting element is curved along a length thereof.

18. The system of claim 16, wherein said inserter instrument includes a proximal handle, an inserter arm extending distally from said handle to a distal end, and said connecting element is engaged to said distal end of said inserter arm.

19. The system of claim 16, wherein said first anchor extension includes an elongated sleeve extending between said proximal and distal ends, said sleeve including at least one elongated opening extending from said distal end thereof toward said proximal end, said elongated opening being oriented toward said second anchor extension, wherein said connecting element is sized to extend through said opening in said predetermined orientation toward said second anchor extension.

20. The system of claim 19, wherein said inserter instrument is engageable to said connecting element between said first and second ends thereof to move said connecting element along said anchor extensions toward said first and second anchors.

21. The system of claim 16, wherein said first and second anchors each include a threaded shaft engageable to the respective first and second vertebral bodies and a receiver at a proximal end of said threaded shaft for receiving the connecting element therein.

22. The system of claim 21, wherein said receiver is pivotal relative to said threaded shaft.

23. The system of claim 16, wherein said anisotropic cross-sectional shape of said connecting element includes a shape selected from the group consisting of: an oval shape, a square shape, a diamond shape, a rectangular shape, a triangular shape, a hexagonal shape, and an octagonal shape.

24. The system of claim 16, wherein said anisotropic cross-sectional shape includes a triangular shape having convexly curved side surfaces extending between vertices of the triangular shape.

25. The system of claim 16, wherein said anisotropic cross-sectional shape includes an I-beam shape with opposite flanges and a central web extending between said flanges.

26. The system of claim 16, wherein:
said connecting element includes a first portion engageable to said first anchor, a second portion engageable to said second anchor, and a transition portion extending between said first and second portions; and
said first portion having a first non-circular cross-sectional shape and said second portion having a second non-circular cross-sectional shape that is different than said first non-circular cross-sectional shape.

27. The system of claim 16, wherein said first moment of inertia is greater than said second moment of inertia.

28. The system of claim 16, wherein said first moment of inertia is less than said second moment of inertia.

29. The system of claim 16, wherein said elongated body is curved between said first and second ends.

30. The system of claim 16, wherein said anisotrpoic cross-sectional shape is uniform between said first and second ends of said elongated body.

* * * * *